United States Patent [19]

Orjales-Venero et al.

[11] Patent Number: 5,672,604
[45] Date of Patent: Sep. 30, 1997

[54] 1-PHENYLMETHYL BENZIMIDAZOLE PIPERAZINE DERIVATIVE

[75] Inventors: Aurelio Orjales-Venero, Neguri; Rosa Rodes-Solanes, Guecho, both of Spain

[73] Assignee: Fabrica Espanola de Productos Quimicos y Farmaceuticos (FAES), Lejona, Spain

[21] Appl. No.: 589,651

[22] Filed: Jan. 22, 1996

Related U.S. Application Data

[63] Continuation of Ser. No. 245,696, May 18, 1994, abandoned.

[30] Foreign Application Priority Data

May 21, 1993 [ES] Spain ..................... 9301104

[51] Int. Cl.$^6$ ..................... A61K 31/495; C07D 403/04
[52] U.S. Cl. ..................... 514/254; 544/370
[58] Field of Search ..................... 544/370; 514/254

[56] References Cited

U.S. PATENT DOCUMENTS

| | | | |
|---|---|---|---|
| 5,106,857 | 4/1992 | Cale, Jr. et al. | 514/322 |
| 5,256,665 | 10/1993 | Orjales-Venero et al. | 514/254 |

FOREIGN PATENT DOCUMENTS

| | | | |
|---|---|---|---|
| 079545 | 5/1983 | European Pat. Off. | |
| 512939 | 11/1992 | European Pat. Off. | 544/370 |
| 49-41198 | 11/1974 | Japan | |
| 126682 | 10/1975 | Japan | 544/370 |
| 918904 | 12/1991 | WIPO | |
| 9207867 | 5/1992 | WIPO | |

OTHER PUBLICATIONS

Iemura et al, *Chem. Pharm. Bull*, 37(10), pp. 2723–2726 (1989).
Iemura et al, *Chem. Pharm. Bull*. 37 (4) pp. 967–972 (1989).
Kodama et al., Chemical Abstracts, vol.84, No.44060 (1976) (Abs. for JP 126682, Oct. 4, 1975).
Hasegawa et al., Chemical Abstracts, vol.82, No.156308 (19).

*Primary Examiner*—Emily Bernhardt
*Attorney, Agent, or Firm*—Birch, Stewart, Kolasch & Birch, LLP

[57] ABSTRACT

New 1-phenylmethyl enzimidazole piperazine derivatives of general formula

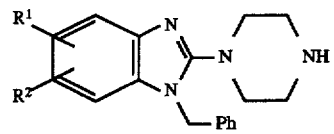

are described wherein $R^1$ and $R^2$ can be a hydrogen atom, a halogen atom, a short chain alkyl group, a nitro group, and a hydroxy group, and their addition salts with pharmaceutically acceptable acids.

These compounds have pharmacological activity as serotonin $5HT_3$ receptor antagonists.

4 Claims, No Drawings

1-PHENYLMETHYL BENZIMIDAZOLE PIPERAZINE DERIVATIVE

This application is a continuation of application Ser. No. 08/245,696, filed on May 18, 1994, abn, the entire contents of which are hereby incorporated by reference.

The present invention relates to new 1-phenylmethylbenzimidazole piperazine derivatives, a process for preparing the same and their addition salts with pharmaceutically acceptable acids. In particular, new compounds of formula (I)

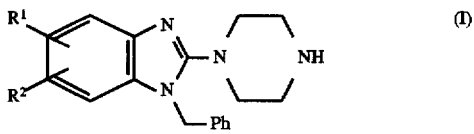

are described wherein $R^1$ and $R^2$ can be a hydrogen atom, a halogen atom, a short chain alkyl group, a nitro group, and a hydroxy group. The short chain refers to a 1 to 3 carbon atom radical, linear or branched, the halogen atoms can be Cl, Br, F or I. This invention similarly comprises the addition salts of these compounds with inorganic acids such as hydrochloric, hydrobromic, phosphoric and sulphuric acids, and organic acids such as acetic, fumaric, tartaric, oxalic and benzoic acids.

Certain benzimidazole derivatives containing piperazine at position 2 in the benzimidazole are known which structurally resemble the compounds of the present invention. Thus U.S. Pat. No. 4,093,726 described compounds of formula (A) with hypotensive activity:

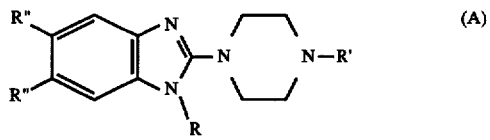

wherein R is an H atom or a methyl group; R' is an alkyl group, an acyl group, an aryl group, an alkoxy carbonyl group, a terahydrofuroyl group, a dialkyl aminocarbonyl group or a furoyl group; R" is a hydrogen atom or a methoxy group. Similarly, patent EP 0,079,545 describes benzimidazole piperazines with antihistaminic activity of general formula (B)

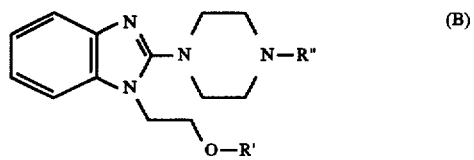

wherein R" is hydrogen or a short chain alkyl group and R' is a short chain alkyl group, an allyl group, a propargyl group or a phenyl group.

Though structurally akin, the foregoing compounds differ from the compounds of the present invention in that the substituent at N 1 in benzimidazole is the phenylmethyl group in all cases. The compounds of the present invention are moreover not always free piperazines, vis. piperazine is never substituted other than by a hydrogen atom at position 4. Both of these facts are very significant from the standpoint of $5HT_3$ antagonist activity of the new derivatives described in the present invention.

The process for preparing the said compounds basically comprises reacting a halogenated derivative of general formula (II)

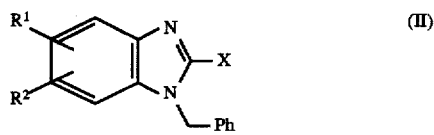

wherein $R^1$ and $R^2$ can be hydrogen, a short chain alkyl group, a halogen atom, a nitro group and a hydroxy group, and wherein X is a halogen, preferably chlorine, with piperazine. Reaction takes place mixing equimolecular quantities of the reagents admitting a piperazine surplus of up to 5 to 1 over the halogenated derivative (II) and heating the reaction mixture to 80°–100° C. for a time interval ranging between five and thirty minutes.

The pharmacological activities of the compounds referred to in this invention were revealed in tests with animals using well established pharmacological processes. Three of the tests made are cited for illustrative purposes and the results set down in Table I.

a) Male and female Wistar rats weighing 180–220 g were anaesthetised with urethane (1.25 g/kg i.p.) and then submitted to cannulation of the trachea, carotid artery and jugular vein, with spontaneous breathing and at a rectal temperature of 37°–38° C. After the arterial pressure (A.P.) and cardiac frequency (C.F.) parameters were stabilised, bradycardia reflex was induced by i.v. injection (the different dose of the drug tested) of 80 μv/kg (1 ml/kg) of serotonin dissolved in sterile physiological serum. Ten minutes later and after taking CF and AP back to constant levels, the products claimed herein were injected i.v. and after a lapse of five minutes, i.v. injection of the serotonin creatinine sulphate complex was repeated, quantifying the inhibition of the Bezold-Jarisch reflex. All the compounds tested displayed activity between 0.3 and 10 μg/kg revealing themselves therefore as serotonin $5HT_3$ receptor antagonists.

b) Guinea pig ileum fragments were submerged in K-H solution at 37° C. pH 7.4, oxygenated with carbogen (95% $O_2$ and 5% $CO_2$) and with an effective preload of 1–2 g. They remained in a stabilization period for 45–60 minutes, and the physiological solution was replaced every 15 minutes. After this time, contractions were induced every 15 minutes, adding 2-methyl-serotonin (final conc.: 10 μmol/l). When contraction intensity was found to be even, the products being tested were added at different concentrations and after incubation for 15 minutes contraction induced by the $5HT_3$ antagonist, 2-methyl serotonin, took place again. The inhibition percentages and CI50 were subsequently calculated (Table I).

c) The inhibition of vomit induced by cis-platinum in a conscious dog was studied. The products were administered intravenously 30 minutes before and 2 hours after cis-platinum (3 mg/kg i.v., 1 ml/kg). A record was made of the number of emetic episodes occurring for five hours after cis-platinum was administered.

The products of the present invention were more active than ondansetron in preventing cis-platinum induced vomit.

TABLE I

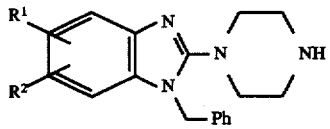

| Product No. | R¹ | R² | 2-me-5HT g.p. ileum CI50 (NM) | B-J reflex rat-anaesth. DE50 (μg/kg iv) | Bind 5HT₃ cort-ento pki |
|---|---|---|---|---|---|
| 1 | Me | H | 28.3 | 1.16 | 8.8 |
| 2 | Cl | H | 7.2 | 2.54 | 9.50 |
| 3 | NO₂ | H | 10.5 | 7.4 | 7.4 |
| 4 | F | H | 1.65 | 1.09 | — |
| 5 | OH | H | 116.5 | 1.33 | — |
| 6 | Cl | Cl | 265 | 16.62 | — |

The results of all the tests show that the compounds of the invention antagonise the action of serotonin at the 5HT₃ receptor level and are hence suitable for preventing vomit induced by anticancerous agents, such as cis-platinum and radiations, and are potentially useful in propyhylaxis and treatment of migraine, anxiety and other neuralgic disorders.

The following example provides further details on the invention without in any way limiting the same.

EXAMPLE 1

Preparing 5-fluoro-1-phenylmethyl-2-piperazinyl-1H-benzimidazole 25 nmoles (2.15 g) of piperazine were added to 5 nmoles (1.4 g) of 2-chloro-5-fluoro-1-phenylmethyl benzimidazole and the mixture heated until both solids fused together, keeping the heat and stirring for 20 minutes. After this time, the reaction mixture was poured onto 100 ml of H₂O, 10% NaOH added, and it was extracted with CH₂Cl₂ (2×100 ml), the organic phase being dried on anhydrous Na₂SO₄ and concentrated at reduced pressure. The oil obtained was purified by flash chromatography using MeOH/CH₂Cl₂: ⅑ as eluant to obtain 1 g of oil which upon being washed with Hexane/ether precipitated as a cream-coloured solid (0.5 g 1.6 nmoles 32% yield) melting at 67°–65° C., its ¹H and ¹³C NMR and the IR spectroscopic data confirming the structure of the product: 5-fluoro-1-phenylmethyl-2-piperazinyl-1H-benzimidazole.

The following were prepared in like wise:
5-chloro-1-phenylmethyl-2-piperazinyl-1H-benzimidazole. Melting point 114°–116° C.
5-hydroxy-1-phenylmethyl-2-piperazinyl-1H-benzimidazole. Melting point 100°–102° C.
5-methyl-1-phenylmethyl-2-piperazinyl-1H-benzimidazole. Melting point 106°–108° C.
5,6-dichloro-1-phenylmethyl-2-piperazinyl-1H-benzimidazole. Melting point 160°–2° C.
5-nitro-1-phenylmethyl-2-piperazinyl-1H-benzimidazole fumarate. Melting point decom >200° C.

We claim:

1. A method of inhibiting vomiting by antagonizing the action at 5HT₃ serotonin receptors which comprises administering an effective amount of a compound having the formula (I):

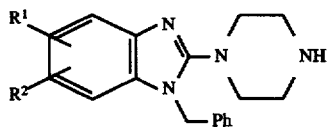

(Formula I)

wherein R¹ is a halogen atom, a nitro group or a hydroxy group, and R² is a hydrogen atom, a halogen atom, a nitro group or a hydroxy group, or a pharmaceutically acceptable salt thereof.

2. The method according to claim 1, wherein said compound is selected from the group consisting of:
5-chloro-1-phenylmethyl-2-piperazinyl-1H-benzimidazole,
5-nitro-1-phenylmethyl-2-piperazinyl-1H-benzimidazole,
5-fluoro-1-phenylmethyl-2-piperazinyl-1H-benzimidazole,
5-hydroxy-1-phenylmethyl-2-piperazinyl-1H-benzimidazole,
5,6-dichloro-1-phenylmethyl-2-piperazinyl-1H-benzimidazole.

3. The method according to claim 1, wherein said compound is (Formula I)

wherein

R¹ is a halogen atom; and

R² is a hydrogen or a halogen atom; or a pharmaceutically acceptable salt thereof.

4. The method according to claim 1, wherein said vomiting is induced by anticancerous agents and/or radiation.

* * * * *